United States Patent
Ignagni et al.

(10) Patent No.: US 7,206,641 B2
(45) Date of Patent: Apr. 17, 2007

(54) MAPPING PROBE SYSTEM FOR NEUROMUSCULAR ELECTRICAL STIMULATION APPARATUS

(75) Inventors: Anthony R. Ignagni, Oberlin, OH (US); Raymond P. Onders, Shaker Heights, OH (US); J. Thomas Mortimer, Russell, OH (US)

(73) Assignee: University Hospitals of Cleveland, Cleveland, OH (US)

( * ) Notice: Subject to any disclaimer, the term of this patent is extended or adjusted under 35 U.S.C. 154(b) by 110 days.

(21) Appl. No.: 10/897,213

(22) Filed: Jul. 21, 2004

(65) Prior Publication Data

US 2005/0107860 A1  May 19, 2005

Related U.S. Application Data

(60) Provisional application No. 60/489,447, filed on Jul. 23, 2003.

(51) Int. Cl.
*A61N 1/00* (2006.01)
(52) U.S. Cl. ............................ 607/115; 607/2; 607/149
(58) Field of Classification Search ................ 607/2, 607/48, 50, 115, 116, 145, 146, 149, 150; 606/41; 600/373, 387
See application file for complete search history.

(56) References Cited

U.S. PATENT DOCUMENTS

| | | | |
|---|---|---|---|
| 3,485,234 A * | 12/1969 | Stevens | 600/434 |
| 3,799,168 A | 3/1974 | Peters | |
| 4,669,471 A | 6/1987 | Hayashi | |
| 4,671,274 A | 6/1987 | Sorochenko | |
| 4,832,048 A * | 5/1989 | Cohen | 606/41 |
| 5,035,696 A | 7/1991 | Rydell | |
| 5,258,006 A * | 11/1993 | Rydell et al. | 606/205 |
| 5,303,703 A | 4/1994 | Monti-Bloch | |
| 5,330,471 A * | 7/1994 | Eggers | 606/48 |
| 5,472,438 A | 12/1995 | Schmit et al. | |
| 5,562,723 A | 10/1996 | Rugland et al. | |
| 5,662,647 A * | 9/1997 | Crow et al. | 606/41 |
| 6,033,400 A | 3/2000 | Grossi et al. | |
| 6,193,718 B1 | 2/2001 | Kortenbach et al. | |
| 6,358,273 B1 | 3/2002 | Strul et al. | |
| 6,379,350 B1 | 4/2002 | Sharkey et al. | |
| 6,391,029 B1 | 5/2002 | Hooven et al. | |
| 6,482,201 B1 | 11/2002 | Olsen et al. | |
| 6,569,119 B1 | 5/2003 | Haberland et al. | |
| 2002/0019631 A1 | 2/2002 | Kidder et al. | |

OTHER PUBLICATIONS

Aiyar, H. et al., "Laparoscopic Identification of the Phrenic Nerves in Humans for Diaphragmatic Pacing," undated, pp. 1-24, Cleveland, Ohio.
International Search Report dated Nov. 19, 2004 of International Application No. PCT/US04/23572 filed on Jul. 21, 2004, 3 pages.
Written Opinion of the International Searching Authority dated Nov. 19, 2004 of International Application No. PCT/US04/23572 filed on Jul. 21, 2004, 4 pages.

* cited by examiner

*Primary Examiner*—Robert Pezzuto
*Assistant Examiner*—Yun Haeng Lee
(74) *Attorney, Agent, or Firm*—Jones Day

(57) ABSTRACT

An apparatus for use with a cannula includes a rigid rod which is receivable and movable in the cannula throughout a range of operative positions in which inner and outer end portions of the rod extend longitudinally outward from the inner and outer ends of the cannula. The apparatus further includes a contact electrode which is configured to be supported on the inner end portion of the rigid rod for movement with the rigid rod through the cannula.

5 Claims, 2 Drawing Sheets

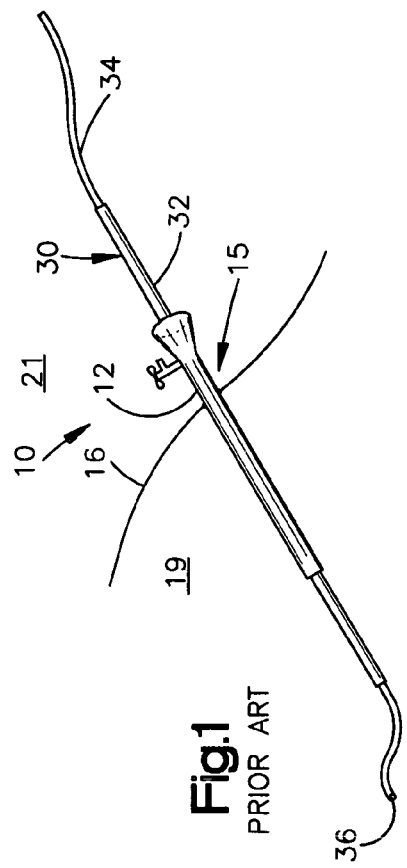
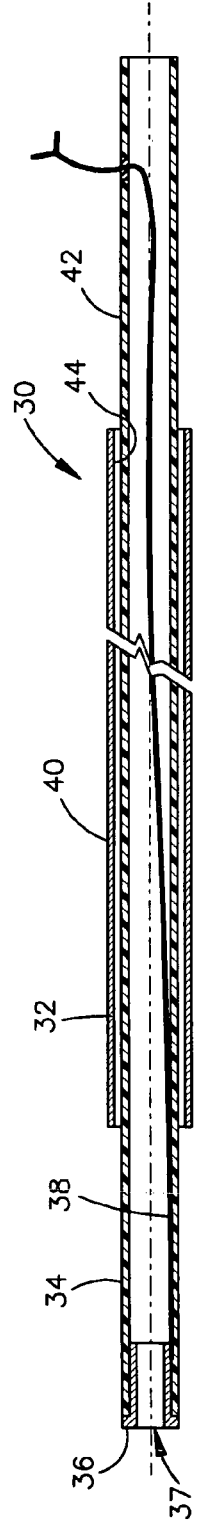
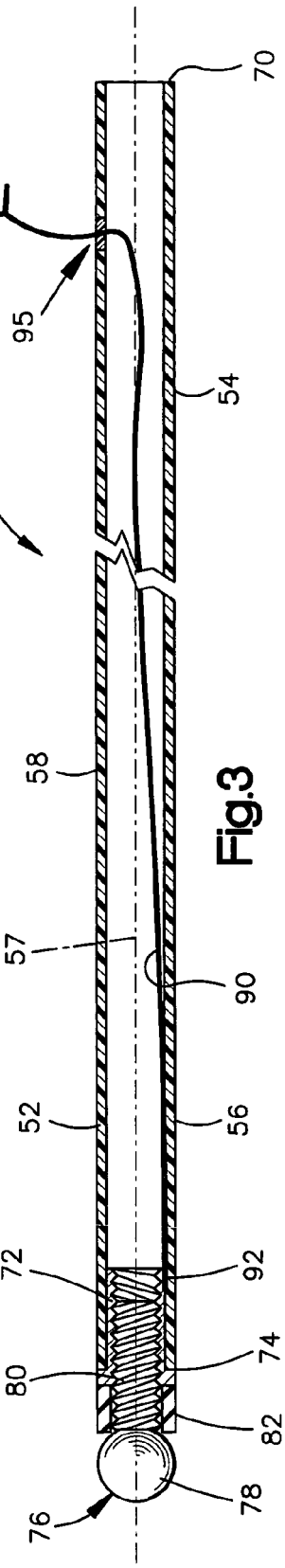
Fig.1 PRIOR ART
Fig.2 PRIOR ART
Fig.3

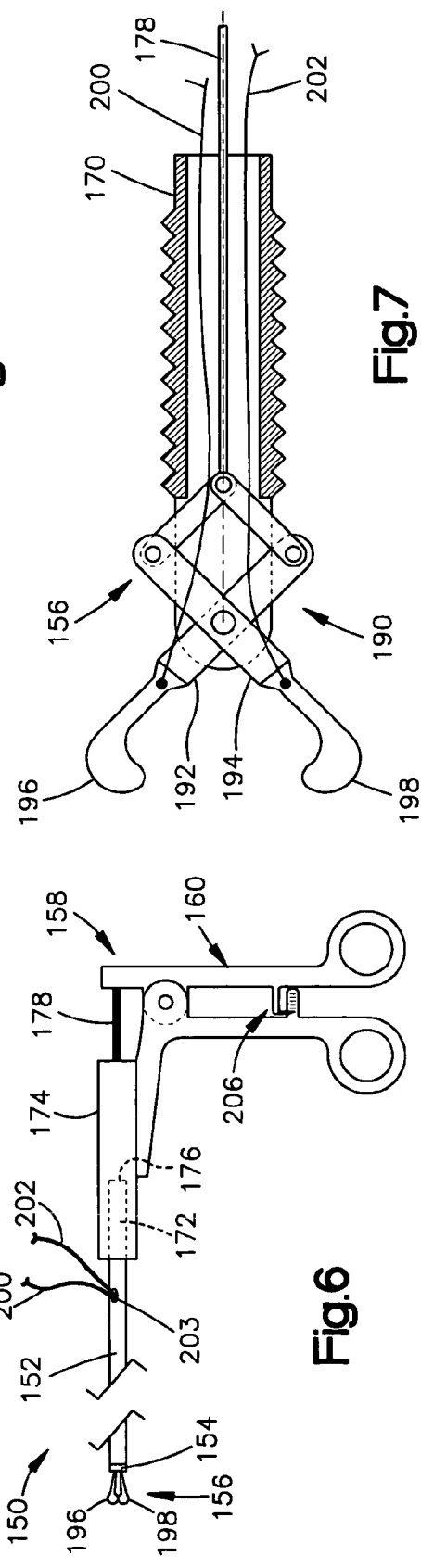

MAPPING PROBE SYSTEM FOR NEUROMUSCULAR ELECTRICAL STIMULATION APPARATUS

RELATED APPLICATIONS

This patent application claims the benefit of provisional U.S. Patent Application No. 60/489,447, filed Jul. 23, 2003, which is incorporated by reference.

TECHNICAL FIELD

This technology relates to the field of neuromuscular electrical stimulation.

BACKGROUND

Neuromuscular electrical stimulation (NMES) involves the controlled stimulation of muscular nerve centers. Known uses of NMES include, for example, the diagnosis of chronic pelvic pain and the installation of a system to produce an effective cough mechanism.

It may be desirable to use minimally invasive surgical techniques for NMES. A minimally invasive NMES apparatus 10 that is known in the prior art is shown schematically in FIGS. 1 and 2. This apparatus 10 includes the cannula portion 12 of a trocar system. The cannula 12 is shown in an operative position in which it extends through an incision 15 in a patient's abdominal wall 16 to communicate the internal peritoneal space 19 with the adjacent external space 21 in the operating room. A trocar (not shown) is first moved through the cannula 12 and pressed against the outer surface of the abdominal wall 16 to form the incision 15 in a known manner. The cannula 12 is then advanced through the incision 15. The apparatus 10 further includes a mapping probe system 30 which is shown in an operative position extending through the cannula 12 from the external space 21 into the peritoneal space 19.

The mapping probe system 30 includes a rigid metal tube 32 which is inserted through the cannula 12 after the trocar is withdrawn from the cannula 12. A flexible plastic tube 34 is then inserted through the rigid metal tube 32. The inner end of the flexible tube 34 is equipped with a contact electrode 36. The outer end of the flexible tube 34 is connected to an operating room vacuum.

As shown in FIG. 2, the electrode 36 is a suction tip electrode. Accordingly, it has an internal passage 37 that serves as a suction port 37 to enable suction in the flexible tube 34 to hold the electrode 36 temporarily against an internal surface at a test site, e.g., a phrenic nerve motor point on the diaphragm muscle. An electrical wire 38 in the flexible tube 34 is part of a known stimulator system that connects the electrode 36 in a pair with a remote electrode (not shown) to provide NMES for characterization and mapping of the electrical response at the internal test site.

As known in the art, the patient's abdomen is inflated by gas pressure provided in the peritoneal space 19. As further known in the art, the cannula 12 grips the rigid tube 32 to form a pneumatic seal that blocks leakage of the inflation gas along a path extending outward through the cannula 12 between the outer surface of the rigid tube 32 and the surrounding inner surface of the cannula 12. The rigid tube 32 is rigid enough to withstand the grip of the cannula 12 without collapsing, but the flexible tube 34, which can bend under the influence of the moving diaphragm muscle, is not. As shown in FIG. 2, a small gap exists between the outer surface 42 of the flexible tube 34 and the surrounding inner surface 44 of the rigid tube 32. This gap provides a flow path that enables the inflation gas to leak from the peritoneal space 19 without passing through the suction-tip electrode 36.

SUMMARY

An apparatus for use with a cannula includes a rigid rod which is receivable and movable in the cannula throughout a range of operative positions in which inner and outer end portions of the rod extend longitudinally outward from the inner and outer ends of the cannula. The apparatus further includes a contact electrode which is configured to be supported on the inner end portion of the rigid rod for movement with the rigid rod through the cannula.

In accordance with a principal feature of the apparatus, the contact electrode is a ball-tip electrode. According to another principal feature, the rigid rod comprises a rigid tube and the contact electrode is a suction-tip electrode. The suction-tip electrode is preferably part of an electrode assembly that includes a flexible tube communicating the suction-tip electrode pneumatically with the rigid tube. Yet another feature includes a pair of bi-polar contact electrodes that are configured to be supported on the inner end portion of the rigid rod for movement with the rigid rod through the cannula, and further includes a mechanism varying the spacing between the bi-polar electrodes.

BRIEF DESCRIPTION OF THE DRAWINGS

FIG. 1 is a schematic view of a prior art NMES apparatus including a mapping probe system.

FIG. 2 is a sectional view of parts of the mapping probe system of FIG. 1.

FIG. 3 is a sectional view of parts of a mapping probe system developed by the inventors.

FIGS. 4 and 5 are views which are similar to FIG. 3, and which show additional parts of the mapping probe system of FIG. 3.

FIG. 6 is a schematic view of parts of another mapping probe system developed by the inventors.

FIG. 7 is an enlarged, partly sectional view of parts of the mapping probe system of FIG. 6.

DETAILED DESCRIPTION

FIGS. 3–7 show mapping probe systems with parts that are examples of the elements recited in the claims. FIG. 3 thus shows a mapping probe system 50 including a rigid rod 52. The rod 52 is receivable through the cannula 12, and is movable longitudinally within the cannula 12 throughout a range of operative positions in which it extends outward from the opposite ends of the cannula 12 in the manner shown in FIG. 1. More specifically, the rod 52 is long enough for an outer end portion 54 of the rod 52 to extend from the cannula 12 into the operating room space 21 sufficiently to be grasped and manipulated manually by a surgeon, and for an inner end portion 56 simultaneously to extend from the cannula 12 into the peritoneal space 19 sufficiently to reach a plurality of internal test sites.

The rod 52 can be made of plastic, metal, a composite material, or any other suitable material. By "rigid" it is meant that the rod 52 will retain a linear or substantially linear configuration centered on a longitudinal central axis 57 when subjected to bending stresses that are ordinarily applied manually during use. Preferably, the rod 52 as a whole is rigid enough not to bend under its own weight when supported from only one end, although it may have a small range of elastic deformation to and from a slightly bowed configuration. Importantly, the rod 52 is rigid enough to withstand the pneumatically sealing grip of the cannula 12 without collapsing.

This particular example of the rod 52 is a cylindrical tube as shown in FIG. 3. The outer diameter of the tube 52 is predetermined with reference to the cannula 12 for establishment of the pneumatic seal between the outer surface 58 of the tube 52 and the surrounding inner surface of the cannula 12.

The terminal outer end 70 of the tube 52 is connectable to the operating room vacuum. An internally threaded metal sleeve 72 is installed at the terminal inner end 74 of the tube 52. A contact electrode 76 has a contact portion in the form of a stainless steel ball tip 78 which is centered on the axis 57, and further has an externally threaded metal stem 80 which is screwed into the metal sleeve 72. The ball tip 78 is receivable through the cannula 12 with the tube 52. As shown in FIG. 3, the diameter of this particular ball tip 78 is equal to the outer diameter of the tube 52. An electrically non-conductive sleeve 82 is received over the stem 80 and extends axially from the ball tip 78 to the metal sleeve 72.

An insulated electrical wire 90 has an uninsulated portion 92 in contact with the metal sleeve 72. The wire 90 extends outward through a pneumatically sealed aperture 95 in the outer end portion 54 of the tube 52 for connection of the electrode 76 in the stimulator system. An optional metal stand-off hinge 96 (FIG. 4) with an additional metal sleeve 98 may be interposed between the ball-tip electrode 76 and the metal sleeve 72 on the tube 52. The mapping probe system 50, when equipped with the ball-tip electrode 76, enables the surgeon initially to coarse map an internal region by sliding the rigid tube 52 longitudinally back and forth within the cannula 12, and thereby to move the ball tip 78 of the electrode 76 into and out of contact with internal test sites in the region being mapped. The surgeon can subsequently map the same region (or a different region) further with the suction-tip electrode 100 shown in FIG. 5.

The suction-tip electrode 100 is part of an electrode assembly 102 that is interchangeable with the ball-tip electrode 76 at the inner end 74 of the rigid tube 52. The electrode assembly 102 includes a cylindrical, flexible plastic tube 104 with inner and outer ends 106 and 108. Like the ball tip electrode 76, the suction tip electrode assembly 102 is movable through the cannula 12 and into the peritoneal space 19 with the inner end portion 56 of the rigid tube 52. A wire 120 within the flexible tube 104 electrically connects the suction-tip electrode 100 at the inner end 106 of the tube 104 with a tubular metal connector 122 at the outer end 108 of the tube 104. An externally threaded stem 124 on the connector 122 can be screwed into the internally threaded sleeve 72 at the inner end 74 of the rigid tube 52. This connects the suction-tip electrode 100 with the rigid tube 52 both electrically and pneumatically.

By "flexible," as opposed to "rigid," it is meant that the flexible tube 104 is not rigid enough to withstand the pneumatically sealing grip of the cannula 12. The flexible tube 104 can bend between its opposite ends 106 and 108 under stresses ordinarily applied manually by the surgeon and/or the moving diaphragm muscle during use, but is preferably able to return elastically to an original, unstressed condition having a linear or substantially linear configuration. The mapping probe system 50, when equipped with the electrode assembly 102, defines a suction air flow path that extends through the flexible tube 104 from the suction-tip electrode 100 to the connector 124, and further through the rigid tube 52 from the connector 122 and the sleeve 72 to the vacuum source at the outer end 70 of the rigid tube 52. The system 50 is free of a leakage flow path along which the abdominal inflation gas can escape the peritoneal space 19 without passing through the suction-tip electrode 100.

Parts of an additional mapping probe system 150 are shown schematically in FIGS. 6 and 7. This system 150 also includes a rigid rod in the form of a tube 152 that is receivable and movable in the cannula 12 throughout a range of operative positions like the operative position shown in FIG. 1. At the inner end of the tube 152 is an internally threaded sleeve 154 which, while preferably having the same configuration as the sleeve 72 described above, may be formed of either electrically conductive or electrically non-conductive material. Other parts of the system 150 include a bi-polar electrode assembly 156 and a manually operated laproscopic instrument 158 with a scissor-action handle 160.

The electrode assembly 156 has an externally threaded sleeve portion 170 (FIG. 7) that is screwed into the internally threaded sleeve 154 at the inner end of the rigid tube 152. When the electrode assembly 156 is mounted on the tube 152 in this manner, it is receivable through the cannula 12 with the tube 152, and is thus movable into and within the peritoneal space 19 with the tube 152.

An outer end portion 172 of the tube 152 is fitted tightly into a barrel portion 174 of the instrument 158. The barrel 174 blocks the abdominal inflation gas from escaping through the outer end of the tube 152. A drive rod 178 extends from the handle 160 of the instrument 158 through the barrel 174 and the tube 152 to a linkage 190 in the electrode assembly 156. The drive rod 178 moves axially to actuate the linkage 190 in accordance with manual manipulation of the handle 160.

The pivotal arms of the linkage 190 include two arms 192 and 194 with electrically uninsulated outer end portions 196 and 198. Those portions 196 and 198 of the arms 192 and 194 are connected to electrical wires 200 and 202 that emerge from an aperture 203 near the outer end portion 172 of the tube 52. The other portions of the linkage 190 are electrically insulated from the sleeve 170, the drive rod 178, and each other. In this arrangement, the outer end portions 196 and 198 of the arms 192 and 194 are electrically connectable in the stimulator system to function as bi-polar electrodes.

The bi-polar electrodes 196 and 198 are spaced apart from each other a distance that can be varied in a controlled manner by manual manipulation of the scissor-action handle 160. Specifically, the handle 160 is shown in a fully closed condition in FIG. 6. As the handle 160 is being opened, the drive rod 178 is moved longitudinally from right to left, as viewed in FIG. 6. This actuates the linkage 190 to move the electrodes 196 and 198 away from one another toward the fully spaced-apart positions shown in FIG. 7. As the handle is again moved back toward the closed condition, the drive rod 178 is moved back from left to right, and the linkage 190 moves the electrodes back toward one another. A locking structure 206 on the handle 160 has a scale that indicates the separation distance between the two electrodes 196 and 198.

Each mapping probe system described above is used in a stimulator system to facilitate the intra-operative location of nerves by NMES while recording the resultant signals. The user interfaces for the stimulator system may include foot switch controls and graphical displays. The information collected by the system may be graphically displayed during a procedure on a computer screen or monitor.

This written description uses examples to disclose the invention, including the best mode, and also to enable a person skilled in the art to make and use the invention. The patentable scope of the invention is defined by the claims, and may include other examples that occur to those skilled in the art. Such other examples, which may be available either before or after the application filing date, are intended to be within the scope of the claims if they have structural elements that do not differ from the literal language of the claims, or if they include equivalent structural elements with insubstantial differences from the literal language of the claims.

The invention claimed is:

1. A monopolar neuromuscular electrical stimulation (NMES) apparatus for use with a cannula and a remote electrode, said apparatus comprising:
   a longitudinally rigid tube configured to be received and moved in the cannula throughout a range of operative positions in which inner and outer end portions of said rigid tube extend longitudinally outward from the inner and outer ends of the cannula;
   a single non-suction contact electrode that is configured to be mounted as a solitary contact electrode at the terminal inner end of said rigid tube to close said inner end, configured to be moved through the cannula with said rigid tube, and configured to be moved into and out of contact with internal test sites to apply NMES at the internal test sites in an electrical circuit with the remote electrode upon movement of said rigid tube back and forth in the cannula; and
   an NMES electrode assembly that is interchangeable with said non-suction contact electrode at said inner end of said rigid tube for said movement with said rigid tube, said electrode assembly comprising a suction tip electrode and a flexible tube configured to communicate said suction tip electrode pneumatically with said rigid tube.

2. An apparatus as defined in claim 1 wherein said suction tip electrode is mounted on said flexible tube at an inner end of said flexible tube, and said electrode assembly further comprises a tubular connector mounted at an outer end of said flexible tube to couple said flexible tube pneumatically with said rigid tube.

3. An apparatus as defined in claim 2 further comprising an electrically conductive structure coupling said suction tip electrode electrically with said tubular connector.

4. An apparatus as defined in claim 3 further comprising a tubular connector mounted at the terminal inner end of said rigid tube to couple said tubular connector in said electrode assembly electrically and pneumatically with said rigid tube.

5. A monopolar neuromuscular electrical stimulation (NMES) apparatus for use with a cannula and a remote electrode, said apparatus comprising:
   a longitudinally rigid rod configured to be received and moved in the cannula throughout a range of operative positions in which inner and outer end portions of said rod extend longitudinally outward from the inner and outer ends of the cannula; and
   a single contact electrode configured to be supported as a solitary contact electrode on said inner end portion of said rigid rod for movement with said rigid rod through the cannula, and configured to be moved into and out of contact with internal test sites to apply NMES at the internal test sites in an electrical circuit with the remote electrode upon movement of said rigid rod back and forth in the cannula;
   wherein said inner end portion of said rigid rod is tubular and has an open inner end, and said contact electrode is configured to close said open inner end of said rigid rod when supported on said inner end portion of said rigid rod; and
   further comprising a suction tip electrode assembly which is interchangeable with said contact electrode at said inner end portion of said rigid rod.

* * * * *